United States Patent [19]
Pischel et al.

[11] Patent Number: 6,166,249
[45] Date of Patent: *Dec. 26, 2000

[54] CREATINE PYRUVATES

[75] Inventors: Ivo Pischel, Tacherting; Stefan Weiss, Trostberg, both of Germany

[73] Assignee: SKW Trostberg Aktiengesellschaft, Trostberg, Germany

[*] Notice: Under 35 U.S.C. 154(b), the term of this patent shall be extended for 21 days.

[21] Appl. No.: 08/893,423

[22] Filed: Jul. 11, 1997

[30] Foreign Application Priority Data

Dec. 20, 1996 [DE] Germany .................. 196 53 225

[51] Int. Cl.$^7$ .................................. C07C 241/00
[52] U.S. Cl. ................................ 562/560; 514/554
[58] Field of Search ........................... 562/560

[56] References Cited

U.S. PATENT DOCUMENTS

| | | | |
|---|---|---|---|
| 1,967,400 | 7/1934 | Fischl | 562/560 |
| 4,548,937 | 10/1985 | Stanko | 514/251 |
| 5,091,171 | 2/1992 | Yu | 424/642 |
| 5,219,846 | 6/1993 | Bru et al. | |
| 5,321,030 | 6/1994 | Kaddurah-Daouk | |
| 5,324,731 | 6/1994 | Kaddurah-Daouk | |
| 5,536,751 | 7/1996 | Bunger | 514/557 |
| 5,627,172 | 5/1997 | Almada | 514/120 |
| B1 5,091,171 | 2/1995 | Yu | 424/642 |
| B2 5,091,171 | 7/1997 | Yu | 424/642 |

FOREIGN PATENT DOCUMENTS

| | | |
|---|---|---|
| 108820 | 11/1982 | European Pat. Off. |
| 0413528 | 2/1991 | European Pat. Off. |
| 669083 | 8/1995 | European Pat. Off. |
| 4508M | 5/1965 | France |
| 94/02127 | 2/1994 | WIPO |
| 96/04240 | 2/1996 | WIPO |

OTHER PUBLICATIONS

Earnest, Acta Physiol. Scand., vol. 153, pp. 207–208, 1995.
Zhyravleva, Chem. Abstract 84:13433c, 1976.
Wilson, Textbook of Organic Medicinal and Pharmaceutical Chemistry, 7th Ed., pp. 69–70, 1977.
Zhuravleva, I.A., Glycolysis and Certain Reactions of the Pentose–Phospate Pathway in DDT–Sensitive and DDT–Resistant House Flies (Musca Domestica L.), Med. Parazitol. Parazit. Bolezni, 1975, and English translation thereof.

*Primary Examiner*—Michael L. Shippen
*Attorney, Agent, or Firm*—Fulbright & Jaworski, LLP

[57] ABSTRACT

Creatine pyruvates are described which have the general formula (I)

$$(\text{creatine})_x(\text{pyruvate})_y(\text{H}_2\text{O})_n \qquad (I)$$

where
 x=1 to 100
 y=1 to 10 and
 n=0 to 10

These creatine pyruvates, which are produced by way of the relatively simple reaction of creatine with pyruvic acid, can be used to enhance long-term performance and strength in the field of sport, to reduce weight and body fat in the field of health, to treat conditions of oxygen deficit (ischemia), obesity and overweight, as food supplements and radical scavenger.

4 Claims, No Drawings

CREATINE PYRUVATES

This patent application relates to creatine pyruvates and their production, the creatine pyruvates being anhydrous or hydrated salts of pyruvic acid and creatine as well as mixtures of these salts with creatine or pyruvic acid.

It is a well known fact that salts of pyruvic acid, which are referred to as pyruvates, have valuable physiological and therapeutic properties for the treatment of various diseases, for example obesity and overweight, and can also be used to prevent the formation of free radicals and to enhance long-term performance (cf. in this context: U.S. Pat. No. 5,508,308, U.S. Pat. No. 5,480,909, U.S. Pat. No. 5,472,980, U.S. Pat. No. 5,395,822, U.S. Pat. No. 5,312,985, U.S. Pat. No. 5,283,260, U.S. Pat. No. 5,256,697, U.S. Pat. No. 4,548,937 and U.S. Pat. No. 4,351,835).

Alkali and alkaline-earth pyruvates are known from the prior art, sodium and potassium pyruvate being unsuitable, however, for therapeutic applications or as food supplements on account of their sodium and potassium ion content respectively. Magnesium and calcium pyruvate, although safe from a physiological point of view, have the distinct disadvantage of not having a sufficiently long shelf life, since magnesium and calcium ions strongly accelerate the decomposition of pyruvic acid and pyruvate ions to form dimers, polymers, cyclic compounds and so on.

The object of this invention is thus to develop forms of pyruvic acid which are physiologically safe and at the same time have a sufficiently long shelf life.

This object was established according to the invention by providing creatine pyruvates having the formula (I)

$$(\text{creatine})_x(\text{pyruvate})_y(\text{H}_2\text{O})_n \quad (I)$$

where x=1 to 100 y=1 to 10 and n=0 to 10.

Depending on the stoichiometric requirements, creatine is present in the compounds of formula (I) in uncharged or cationic form and pyruvate as pyruvic acid or as anion.

Surprisingly, it was found that the creatine pyruvates of the invention have a long shelf life, although pyruvic acid is a very unstable 2-oxocarboxylic acid and the known salts of creatine decompose readily to form creatinine. Since creatine occurs as an internal salt and is only a weak base, it was not predictable that stable creatine salts can be prepared from monocarboxylic acids. According to the prior art, namely, only creatine salts of strong di- and polycarboxylic acids were known hitherto (cf. WO 96/04 240)

The creatine pyruvates of the invention, having the general formula (I), contain the physiologically safe creatine cation of formula (II).

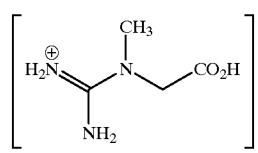

(II)

Creatine is not only an endogenous substance and a valuable food supplement but also has valuable therapeutic properties. It has been known for over 100 years as a muscular substance and serves as a source of energy for the muscle. It was shown in a series of scientific studies that the intake of creatine can lead to an increase in muscular tissue and muscular performance. There are also scientific findings which indicate that the pancreas releases more insulin under the influence of creatine. Insulin promotes the uptake of glucose and amino acids by muscle cells and stimulates protein synthesis. Insulin also lowers the rate of protein catabolism.

The pyruvate anion in the creatine pyruvates of the invention usually assumes the structure of formula (III).

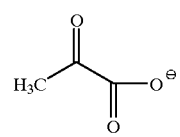

(III)

In those creatine pyruvates which contain water of crystallization the pyruvate anion can also assume the 2,2-dihydroxy form according to formula (IV):

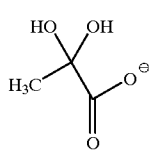

(IV)

The creatine pyruvates according to the invention comprise salts which preferably contain the creatine cation and the pyruvate anion or the 2,2-dihydroxypropionate anion in a molar ratio of 1:1 or a molar ratio of approximately 1:1. The compounds of the invention may also be mixtures of these salts with creatine or pyruvic acid.

The creatine pyruvates of the invention can be produced by way of the relatively simple reaction of creatine with pyruvic acid in the temperature range from −10 to 90° C., preferably in the temperature range from 10 to 30° C. The creatine and pyruvic acid are reacted here in a molar ratio of 100:1 to 1:10, preferably 5:1 to 1:2. For this reaction creatine can be used in the anhydrous form, as monohydrate or as wet product. The pyruvic acid may be used as anhydrous acid or in the form of an aqueous solution.

The reaction may be carried out in the presence or absence of a solvent or diluting agent. A broad range of polar solvents is suitable as solvent or diluting agent. Preference is given to alcohols (such as methanol, ethanol, isopropanol or cyclohexanol), ethers (such as diethyl ether, tetrahydrofuran, 1,4-dioxane or ethylene dimethyl ether), ketones (such as acetone, methyl ethyl ketone or cyclohexanone), esters (such as methyl acetate, ethyl acetate or ethyl formate) or mixtures thereof.

The reaction can be carried out using customary technical apparatus such as mixers, blade driers and agitating vessels.

The creatine pyruvates with water of crystallization are obtained by adding water during or after the reaction of pyruvic acid with creatine and/or by using aqueous creatine and/or aqueous pyruvic acid. The scope of this invention also allows for the addition—during or after production of the creatine pyruvates—of other substances too, such as pharmaceutical formulation additives, vitamins, mineral substances, trace elements, carbohydrates such as glucose, dextrose, or maltose and amino acids such as L-carnitine or other food supplements.

The subject matter of the invention thus also comprises physiologically compatible compositions which contain creatine pyruvates and at least one additional, physiologically compatible substance selected from the group comprising pharmaceutical adjuvants or carriers, vitamins, mineral substances, carbohydrates, amino acids or other food supplements.

By virtue of their optimum properties such as that of being physiologically safe, having a long shelf life, being highly soluble in water and having good bioavailabilty, the creatine pyruvates of the invention are excellently suited for therapeutic applications in medicine and as food supplements, exhibiting the valuable biological and medical properties both of pyruvates and of creatine.

Surprisingly, the creatine pyruvates of the invention exhibit marked synergistic effects when used in medicine and as food supplements. They are especially suitable in this context for treating conditions of oxygen deficit (ischemia) and overweight and obesity, since the breakdown of muscular substance during the treatment is reduced; the muscle-enhancing effect of creatine pyruvate is particularly important in the case of dietary cures. They also prevent the formation of free radicals and scavenge free radicals or oxidizing species of oxygen. The synergistic effects are also especially evident when creatine pyruvate is used in the field of sport to enhance long-term performance.

The following examples serve to explain the invention in more detail.

EXAMPLES

Example 1

26.4 g (0.3 mol) pyruvic acid are dissolved at room temperature in 100 ml of ethyl acetate. 26.2 g (0.2 mol) creatine are added to this solution and the mixture agitated for 4 hours. Then the white, finely crystalline product is separated out by filtering and washed twice with 25 ml of ethyl acetate. It is dried for 4 hours at 50° C. in a vacuum-drying chamber. The yield is 95.0%. The creatine pyruvate (1:1) melts at 106 to 110° C. and decomposes (capillary).

$C_7H_{13}N_3O_5$, calculated: C 38.36%, H 5.94%, N 19.18%; found: C 38.23%, H 6.06%, N 19.28%; IR (KBr) [1/cm]: 620, 829, 880, 976, 1049, 1110, 1177, 1209, 1269, 1354, 1404, 1605, 1663, 1697, 1734, 1763, 2518, 2593, 3147, 3397; $^1$H-NMR ($D_2O$, 300 MHz): δ=2.34 (s, 3H, MeCO), 3.08 (s, 3H, Me-N), 4.06 (s, 2H, $CH_2$); HPLC content: creatine 59.8%, pyruvic acid 40.2%.

Example 2

26.2 g (0.2 mol) creatine are mixed with 17.6 g (0.2 mol) pyruvic acid in a mortar. The mixture becomes increasingly viscous and ultimately solidifies to a white, finely crystalline product. The yield is quantitative (>99%). The creatine pyruvate (1:1) melts at 109 to 114° C. and decomposes (capillary).

Example 3

29.8 g (0.2 mol) creatine monohydrate are mixed intimately with 35.2 g (0.4 mol) pyruvic acid in a glass beaker. The mixture is left to stand, ultimately solidifying to a white, finely crystalline product. It is ground in a mortar and dried for 4 hours at 50° C. in a vacuum-drying chamber. The yield is quantitative (>99%). The creatine pyruvate obtained in this way (1:2) melts at 90–95° C. and decomposes (capillary).

Example 4

29.8 g (0.2 mol) creatine monohydrate are mixed in a mortar with 8.8 g (0.1 mol) pyruvic acid and 20 ml of tetrahydrofuran added. The mixture becomes increasingly viscous and ultimately solidifies to a white, finely crystalline product which is dried for 4 hours at 50° C. in a vacuum-drying chamber. The yield is quantitative (99%). The creatine pyruvate (2:1) melts at 118 to 120° C. and decomposes (capillary).

What is claimed is:

1. Creatine pyruvate wherein the ratio of creatine to pyruvate is 1:1 and the creatine pyruvate contains 0 to 10 moles of water.

2. The creatine pyruvate of claim 1 in anhydrous form.

3. Creatine 2,2-dihydroxypropionate wherein the ratio of creatine to 2,2-dihydroxypropionate is 1:1 and the creatine 2,2-dihydroxypropionate contains 0 to 10 moles of water.

4. The creatine 2,2-dihydroxypropionate of claim 3 in anhydrous form.

* * * * *

UNITED STATES PATENT AND TRADEMARK OFFICE
CERTIFICATE OF CORRECTION

PATENT NO. : 6,166,249
DATED : December 26, 2000
INVENTOR(S) : Pischel, et. al.

It is certified that error appears in the above-identified patent and that said Letters Patent is hereby corrected as shown below:

In <u>cover page</u>, in the section entitled <u>U.S. Patent Documents</u>, change "2/1995" to - - 9/1995 - -.

Signed and Sealed this

First Day of May, 2001

Attest:

NICHOLAS P. GODICI

*Attesting Officer*     *Acting Director of the United States Patent and Trademark Office*